United States Patent [19]

Griffith et al.

[11] 4,351,847
[45] Sep. 28, 1982

[54] ANTIVIRAL ALPHA, ALPHA-DIALKYL ADAMANTYLETHYLAMINES

[75] Inventors: Ronald C. Griffith, Pittsford; Clyde R. Kinsolving, Fairport, both of N.Y.

[73] Assignee: Pennwalt Corporation, Philadelphia, Pa.

[21] Appl. No.: 277,777

[22] Filed: Jun. 26, 1981

[51] Int. Cl.³ ............................................. A61K 31/13
[52] U.S. Cl. ................................................... 424/325
[58] Field of Search ........................................ 424/325

[56] References Cited

U.S. PATENT DOCUMENTS 3,352,912 11/1967 Prichard .............................. 424/325
4,100,170 7/1978 Shetty ................................. 424/325

*Primary Examiner*—Jerome D. Goldberg

[57] ABSTRACT

Warm-blooded animals are treated by administering to the animal a dosage, effective to prevent or to alleviate the symptoms of herpes virus, type II, of a compound of the formula I or its acid salt:

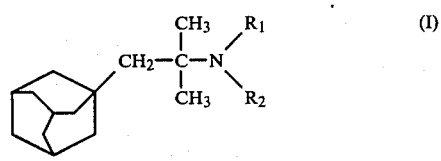

wherein $R_1$ and $R_2$ are selected from the class consisting of H and $-CH_3$; and at least one pharmaceutically acceptable carrier, wherein the compound is 0.01 to 95% by weight of the composition.

6 Claims, No Drawings

ANTIVIRAL ALPHA, ALPHA-DIALKYL ADAMANTYLETHYLAMINES

BACKGROUND OF THE INVENTION

The invention relates to an antiviral composition and a method of preventing or treating herpes virus, type II in warm-blooded animals with the antiviral composition. More particularly, the invention comprehends an antiviral composition containing alpha,alpha-dialkylethylamine derivatives of adamantane and at least one pharmaceutically acceptable carrier used to treat warm-blooded animals infected with (or to prevent infection with) the herpes virus, type II.

Herpes II is a form of herpes virus that causes a highly infectious venereal disease which is marked by painful lesions in the genital area. In its other forms, herpes causes maladies ranging from common cold sores, chicken pox, and shingles to infectious mononucleosis, and rarer diseases including hepatitis and encephalitis. Reactions to the herpes II infections can range from minor discomfort to incapacitating pain. The disease poses health threats to women and the newborn. There is a high correlation between genital herpes infections and cervical cancer. The newborn child is endangered if birth takes place during an eruptive episode of the disease; there is particular danger to the ocular, labial and genital areas; and skin infections are also common. Blindness and death in the newborn child are not infrequent. Physicians usually resort to delivery of the baby by cesarean section.

U.S. Pat. Nos. 3,270,036, 3,489,802 and 3,501,511 teach various adamantylamine and adamantylalkylamine derivatives as being useful as hypoglycemic agents and antiviral agents for specific viruses, usually influenza, vaccinia, and arbovirus, but never for herpes. In clinical practice, those adamantyl alkyl amines have shown utility only against influenza viruses and only if treatment is prophylactic; treatment after the infection is ineffective.

U.S. Pat. No. 4,100,170 teaches adamantylethylamines that are useful as anorexic agents.

No art is known which discloses the use of alpha,alpha-dialkyl adamantylethylamines for the treatment of herpes II or which discloses their utility to treat the virus while the animal is infected.

SUMMARY OF THE INVENTION

This invention is directed to:

A. A pharmaceutical composition in unit dosage form comprising (i) an amount effective to prevent or to alleviate the symptoms of herpes virus, type II, in warm-blooded animals of a compound of the formula I or its acid salt:

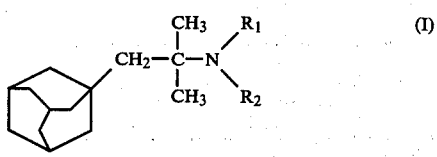

wherein $R_1$ and $R_2$ are selected from the class consisting of H and $-CH_3$ (, preferably H), and (ii) at least one pharmaceutically acceptable carrier, wherein the compound is from about 0.01 to about 95% by weight of the composition. The identity of the acid forming the salt of the amine is not critical. The hydrochloride of the amine is preferred, but any pharmaceutically acceptable inorganic or organic acid such as the sulfate, acetate, nitrate or the like may be used.

B. A method for preventing or treating herpes II in warm-blooded animals comprising administering to animals a dosage of the composition of A, supra, in an amount effective to prevent or alleviate the symptoms of the infection.

DETAILED DESCRIPTION OF THE INVENTION

The adamantane drug (I) of this invention can be administered in the antiviral treatment according to this invention by any means that effects contact of the active ingredient compound (I) with the site of virus infection in the body, either before or after the infection sets in. For example, a dosage form of the drug may be used for oral, topical, parenteral, ophthalmic, nasal, aural, rectal, vaginal or urethral application or on other specific parts of the body (the preferred application form is topical). The dosage form may be a solution, gel, emulsion, lozenge, suspension, paste, ointment, suppository, tablet, capsule, powder, granule or an aerosol product or other suitable formulation (preferably ointment). The dosage administered will be dependent upon the virus (i.e., herpes II) being treated, the weight of the recipient, the frequency of treatment and the effect desired. Generally in a man, a daily internal or topical dosage of active ingredient compound (I) will be from about 10 to 500 milligrams although lower and higher amounts can be used. The active ingredient, the drug, can be employed in useful compositions according to the present invention in such dosage forms as solution, semisolid, solid and aerosol forms. These dosage forms preferably deliver from about 1 mg to 500 mg of active ingredient, with the range from 10 mg to about 200 mg being most preferred. In these dosage forms the antiviral composition will contain at lease one non-toxic pharmaceutically acceptable carrier for the active ingredient. Examples of the non-toxic carriers or adjuvants are viscosity enhancers such as bentonite, celluloses (e.g., methylcellulose, ethylcellulose, and carboxy methylcellulose) tragacanth, glyceryl monostearate, cetyl alcohol, stearyl alcohol, synthetic spermaceti and stearic acid; pH modifiers such as dibasic sodium phosphate, citric acid, and sodium hydroxide; preservatives such as methyl paraben, propyl paraben, benzoic acid, and benzyl alcohol; sweeteners such as saccharin, sorbitol (D-glucitol), and mannitol; stability enhancers such as sodium bisulfite and ascorbic acid; coloring agents such as food, drug and cosmetic (FD&C) and drug and cosmetic (D&C) colors certified by the Food and Drug Administration (FDA); solvents such as water, alcohol (e.g., ethyl alcohol (for internal use) and isopropyl alcohol (for external use)), and propylene glycol; suspending agents such as kaolin, celluloses (e.g., methylcellulose, ethylcellulose and carboxy methylcellulose), acacia, and tragacanth; granulating agents such as acacia, sucrose, and polyvinylpyrrolidone (PVP); coating agents such as celluloses (e.g., ethylcellulose and propylcellulose) and PVP; disintegration/dissolution modifiers such as starch (e.g., corn starch, rice starch and potato starch) and polysorbate 80 (polyoxyethylene (20) sorbitan monooleate); excipients such as lactose, starch, and cellulose; propellents such as isobutane, fluorocarbon 11 (trichlorofluoro methane), fluorocarbon 12 (dichlorodifluoro methane); ion exchange agents such as XE-69 and IR 120 (sulfonic acid cation resins (styrene divinyl benzene) and IRP 58 (a phenolic polyamine anion exchange resin); emulsifying agents such as glyceryl stearate (self emulsifying), sorbitan stearate, decyloleate, cetearyl alcohol, polysorbate 60 and triethanolamine; and humectants such as myristyl myristate.

Typical embodiments of the pharmaceutical composition of this invention are: (all percentages are by weight of composition)

1. Tablet:

| | |
|---|---|
| drug | 100 mg |
| microcrystalline cellulose | 100 mg |
| magnesium stearate | 5 mg |

2. Capsule:

| | |
|---|---|
| drug | 100 mg |
| lactose | 100 mg |
| starch | 5 mg |
| magnesium stearate | 2 mg |

3. Oral Solution:

| | |
|---|---|
| drug | 2 g |
| sorbitol (D-glucitol) solution 70% | 50 ml |
| citrus flavor | 5 ml |
| citric acid | 1 g |
| distilled water, quantity sufficient to make (q.s. ad) | 100 ml |

4. Parenteral Solution:

| | |
|---|---|
| drug | 2.5 g |
| benzyl alcohol | 0.1 g |
| sterile distilled water, q.s. ad | 100 ml |

5. Ophthalmic Ointment:

| | |
|---|---|
| drug | 1 g |
| polyethylene glycol ointment, N.F., q.s. ad | 100 g |

6. Aerosol Spray:

| | |
|---|---|
| drug | 5% |
| polysorbate 20 (polyoxyethylene 20 sorbitan monolaurate) | 0.1% |
| propellent 11/12, 40/60 ratio by weight, q.s. ad | 100% |

7. Topical Lotion:

| | |
|---|---|
| drug | 5% |
| mineral oil | 30% |
| polysorbate 80 | 10% |
| propylene glycol | 5% |
| white petrolatum | 5% |
| benzoic acid | 2% |
| perfume | 0.1% |
| water q.s. ad | 100% |

8. Topical Ointment:

| | |
|---|---|
| drug | 5% |
| hydrophilic ointment U.S.P. q.s. ad | 100% |

9. Oral Resinated Suspension (sustained release):

| | |
|---|---|
| drug resinate | 10% |
| (drug content of resin is | 15%) |
| ketrol (xanthan gum) | 10% |
| saccharin | 0.5% |
| flavor | 0.2% |
| sorbitol 70% solution | 50% |
| methylparaben | 0.5% |
| water, q.s. ad | 100% |

10. Oral Resinated Capsule (sustained release):

| | |
|---|---|
| drug resinate | 200 mg |
| (drug content of resin is | 50%) |
| lactose | 100 mg |
| magnesium stearate | 5 mg |

11. Topical Gel:

| | |
|---|---|
| drug | 5% |
| carbopol 934 (carboxypolymethylene) | 1% |
| alcohol | 10% |
| triethanolamine | 0.8% |
| polyethylene glycol 300 | 30% |
| water q.s. ad | 100% |

12. Ophthalmic Solution:

| | |
|---|---|
| drug | 2.5% |
| benzyl alcohol | 0.1% |
| sterile distilled water, q.s. ad | 100% |

13. Oral Lozenge:

| | |
|---|---|
| drug | 5% |
| sugar | 75% |
| gelatin | 5% |
| flavor | 1% |
| water q.s. ad | 100% |

Note that "drug" in each of the above examples is an alpha,alpha-dimethyl adamantylethylamine of the instant invention.

Preferred pharmaceutical compositions of this invention are as follows:

Ointment 1

| | |
|---|---|
| Glyceryl Stearate self emulsifying | 7.0% |
| Glyceryl Monostearate | 3.0% |
| Decyl Oleate | 3.0% |
| Myristyl Myristate | 2.0% |
| Cetearyl Alcohol and Ceteareth | 4.0% |
| Cetyl Alcohol | 5.0% |
| Stearyl Alcohol | 4.0% |
| Synthetic Spermaceti | 2.0% |
| Propyl paraben | 0.07% |
| Methyl paraben | 0.30% |
| Adamantylethylamine HCl | 4.7% |
| Purified water q.s. | 100% |

Ointment 2

| | |
|---|---|
| Polysorbate 60 | 3.0% |
| Sorbitan Stearate | 3.0% |
| Stearic Acid | 10.0% |
| Triethanolamine | 0.25% |
| Propylene Glycol | 10.0% |
| Adamantylethylamine HCl | 4.7% |
| Purified water q.s. | 100% |

Ointment 3

| | |
|---|---|
| Bentone Gel IPM* or M10** | 47.5% |
| Span 85*** | 19.0% |
| Polysorbate 80 | 10.0% |
| Adamantylethylamine HCl | 4.7% |
| Purified water q.s. | 100% |

*Isopropyl Myristate, Stearalkonium Hectorite Propylene Carbonate (NL Industries)
**Mineral Oil, Quaternium-18 Hectorite, Propylene Carbonate (NL Industries)
***Sorbitan Trioleate

EXAMPLE 1

The hydrochloride salt of the compound of Formula (I) wherein $R_1$ and $R_2$ are hydrogen was tested for its antiviral activity against herpes II using a method that was developed by Sidwell.[1,2]

[1] L. B. Allen, C. Hintz, S. M. Wolf, J. H. Huffman, R. K. Robbins, R. W. Sidwell. H. Infect. Dis. 133: A178–A183 (1976).
[2] L. B. Allen, S. M. Wolf, C. J. Hintz, J. H. Huffman and R. W. Sidwell. Ann. N.Y. Acad. Sci. 284: 247–253, 1977.

Female mice were inoculated with herpes II for producing intravaginal lesions. The mice were then divided up into groups of five mice per group. Four hours after inoculation with the virus, the drug treatment was begun; the drug was applied topically at different dosages per group in the following cream base:

| | |
|---|---|
| Bentone Gel-IPM[a] | 41.2% |
| Span 85[b] | 16.4% |
| Polysorbate 80[c] | 8.6% |
| Water Deionized qs to | 100%. |

[a] Bentonite suspended in isopropyl myristate
[b] Sorbitan trioleate
[c] Polyoxyethylene (20) sorbitan monooleate The amount of the drug in the cream base applied to the mice was 1% for one group and 4.1% (each based on the weight of the cream) for another. Each animal in a group was dosed with the same amount of the drug three times a day for six days. A placebo of the cream base (control) dosage was used in the same manner as mentioned above on a third group of mice. The cream was applied by intravaginal administration in an amount of 0.1 ml per dose. The animals were observed each day for the six day period and lesions, when visible, were measured and scored.

All of the animals were observed and scored by the same person who equated the severity of the lesion in the animal with a number. A scale of 0 to 4 was used to score the animals where 0 meant that no lesion was formed (i.e., normal); 1 meant that a 1–2 mm perivaginal redness and swelling had developed; 2 meant that a 2–3 mm perivaginal redness and swelling had developed; 3 meant that a 3–4 mm perivaginal and perianal redness and swelling had developed; and 4 meant that a greater than 4 mm perivaginal and perianal redness and swelling with discharge had developed.

Calculations for antiviral activity of the drug were based on the average of the daily average scores for the fourth, fifth and sixth days for each group of animals. The difference between the control group and the test group is termed the inhibition score which is a measure of the drug's antiviral activity and is expressed as percentage. In the group where the percent active ingredient in the cream was 1%, the drug was applied in equal amounts three times a day to provide a daily total application of 150 mg of active ingredient for every kg of the animal's body weight; the inhibition score recorded was 23%.

Where the percent active ingredient in the cream base was 4.1%, the same test procedure was followed to provide a total daily application of 615 mg of active ingredient per kg of animal weight and the inhibition score was 41%.

EXAMPLE 2

The hydrochloric acid salt of the compound (drug) of Formula (I) wherein $R_1$ and $R_2$ are methyl groups was tested for its antiviral activity against herpes II using the same method as in Example 1. In the group of mice where the strength of active ingredient (drug) in the cream base was 1% and the total daily application was in an amount of 150 mg/kg, the inhibition score was zero. However, where the cream base contained 4.2% of the drug and was applied in a total daily amount of 630 mg/kg, the inhibition score was 27%.

Comparative tests were run using close analogues to those found effective in the present invention and other compounds in the literature reported to have antiviral activity. The analogues tested were (A) the hydrochloric acid salt of the compound of Formula (I) wherein $R_1$ and $R_2$ are hydrogen and one of the alpha methyl groups is replaced by hydrogen and (B) the compound of Formula (I) wherein $R_1$ and $R_2$ are hydrogen and both of the alpha methyl groups are replaced by hydrogen. The strengths and application rates used (following the technique of Example 1) are reported in the following Table:

TABLE 1

| Analogue | Strength | Total Daily Application Rate |
|---|---|---|
| A | 1% | 150 mg/kg |
| A | 4.2% | 630 mg/kg |
| B | 1% | 150 mg/kg |
| B | 4.0% | 735 mg/kg |

The inhibition score for these analogues was zero.

The known antiviral compounds, rimantadine, amantadine, and ribavirin, were tested following the same technique as described in Example 1. The strengths and application rates used are reported in the following Table:

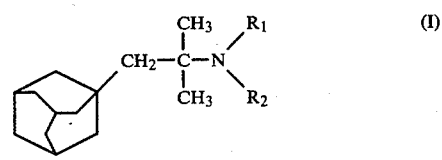

| Antiviral Agent | Formula | Strength | Total Daily Appln. Rate (mg/kg) |
|---|---|---|---|
| Rimantadine | | 1% | 150 |
| Rimantadine | (adamantyl-CH(CH₃)-NH₂·HCl) | 4.6% | 690 |
| Amantadine | | 1% | 150 |
| Amantadine | (adamantyl-NH₂) | 5% | 750 |
| Ribavirin | (ribavirin structure) | 5% | 750 |

Rimantadine and amantadine had an inhibition score of zero. Ribavirin had an inhibition score of 18%.

What is claimed:

1. A method for treating herpes II virus in a warm-blooded animal comprising administering to the animal in need of said treatment an effective amount for treating the herpes II virus of a composition comprising (i) a compound of the formula I or its acid salt:

(adamantyl-CH₂-C(CH₃)₂-N(R₁)(R₂))  (I)

wherein $R_1$ and $R_2$ are selected from the class consisting of H and —CH$_3$ and (ii) at least one pharmaceutically acceptable carrier, wherein the compound is 0.01 to 95% by weight of the composition.

2. The method of claim 1 wherein the acid salt of the compound is hydrochloride.

3. The method of claim 2 wherein the composition is administered to the warm-blooded animals by physically applying the composition to the affected area.

4. The method of claim 3 wherein the composition applied to the affected area is in the form of a cream.

5. The method of claim 3 wherein the composition applied to the affected area is in the form of an ointment.

6. The method of claim 3 wherein the composition applied to the affected area is in the form of a solution.

* * * * *